United States Patent [19]
Santi et al.

[11] Patent Number: 5,948,873
[45] Date of Patent: Sep. 7, 1999

[54] METALLOCENES, THEIR PREPARATION AND USE IN THE POLYMERIZATION OF ALPHA-OLEFINS

[75] Inventors: Roberto Santi; Giampietro Borsotti, both of Novara; Paolo Biagini, Trecate; Gabriele Lugli, S. Donato Mil.se; Viviano Banzi, Viagarano Mainarda, all of Italy

[73] Assignee: Enichem S.p.A., Milano, Italy

[21] Appl. No.: 08/994,568

[22] Filed: Dec. 19, 1997

[30] Foreign Application Priority Data

Dec. 19, 1996 [IT] Italy .................. MI96/A2661

[51] Int. Cl.$^6$ .............. C08F 4/18; C07F 17/00; C07F 7/00
[52] U.S. Cl. ............... 526/129; 526/160; 526/943; 502/103; 502/117; 556/11; 556/12; 556/53
[58] Field of Search ................. 556/11, 12, 53, 556/943; 526/129, 160, 943; 502/103, 117

[56] References Cited

FOREIGN PATENT DOCUMENTS 490256  6/1992  European Pat. Off. .
611773  8/1994  European Pat. Off. .

OTHER PUBLICATIONS

Chemical Abstracts, vol. 123, No. 19, Nov. 6, 1995, Abstract No. 256897, Hitchcock, S.R., et al: Synthesis of Ansa–Titanocenes from 1,2–Bis(2–Indenyl)Ethane and Structural Comparison in the Catalytic Epoxidation of Unfunctionalized Alkenes. Organometallics, vol. 123, No. 8, 1995, p. 1177.

*Primary Examiner*—Porfirio Nazario-Gonzalez
*Attorney, Agent, or Firm*—Oblon, Spivak McClelland, Maier & Neustadt, P.C.

[57] ABSTRACT

Catalytic component for the copolymerization of ethylene with alpha-olefins having general formula (I):

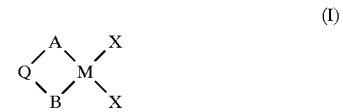

(I)

wherein:

A is a cyclopentadienyl derivative having general formula (II)

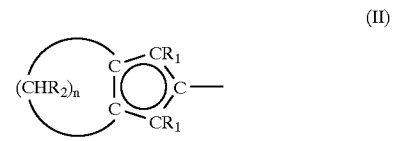

(II)

B is selected from:
1) any of the cyclopentadienyl derivatives A defined above
2) a monofunctional cyclopentadienyl radical (F) selected from cyclopentadienyl, indenyl, fluorenyl and the relative alkyl, aryl, trialkylsilyl substituted derivatives;

Q, a bridge between A and B, is a bifunctional radical.

21 Claims, 2 Drawing Sheets

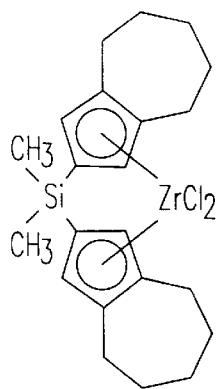 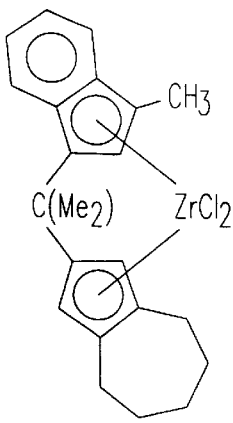 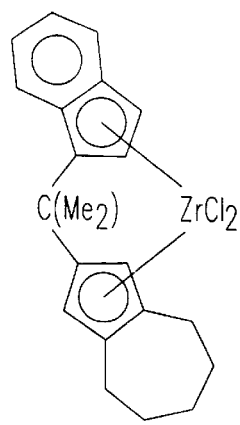 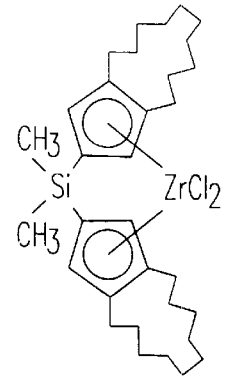
*FIG.1.1*   *FIG.1.2*   *FIG.1.3*   *FIG.1.4*
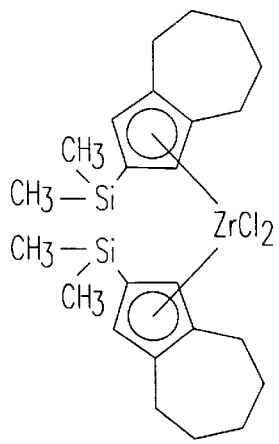 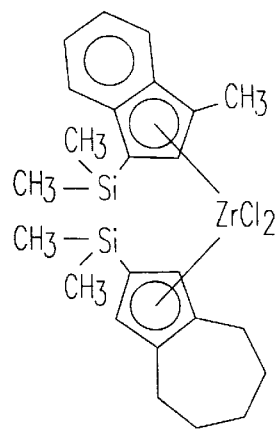 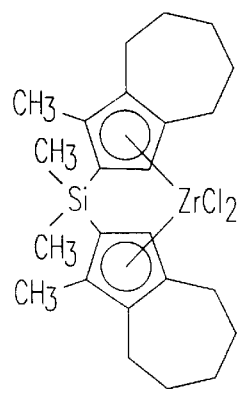
*FIG.1.5*   *FIG.1.6*   *FIG.1.7*

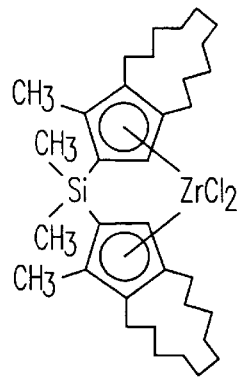
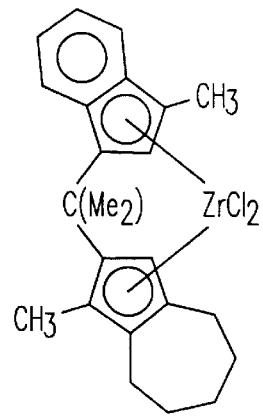
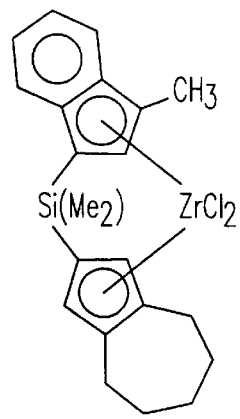
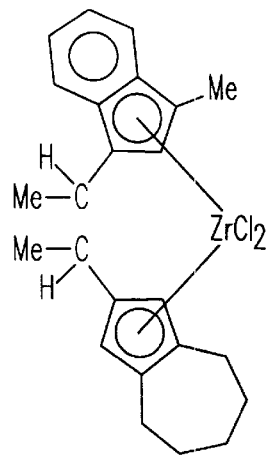
*FIG. 1.8*  *FIG. 1.9*  *FIG. 1.10*  *FIG. 1.11*
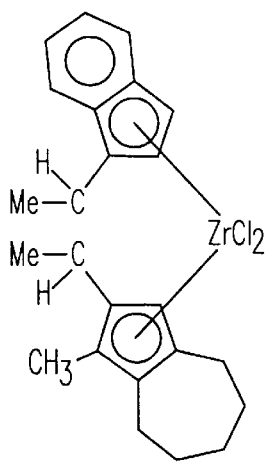
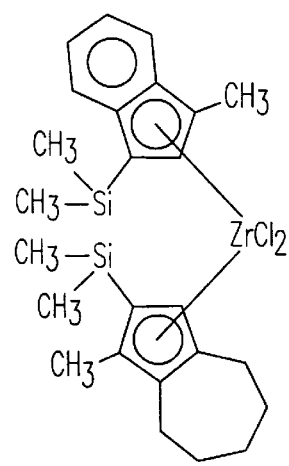
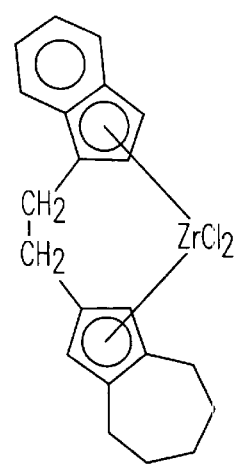
*FIG. 1.12*  *FIG. 1.13*  *FIG. 1.14*

METALLOCENES, THEIR PREPARATION AND USE IN THE POLYMERIZATION OF ALPHA-OLEFINS

The present invention relates to catalytic components of the metallocene type and their use in the preparation of (co)polymers of $C_2$–$C_{20}$ olefins, particularly copolymers of ethylene with $C_3$–$C_{20}$, preferably $C_3$–$C_{10}$, even more preferably $C_3$, alpha-olefins, possibly in the presence of a diene.

Metallocenes having as ligands derivatives of cyclopentadienyl are known as catalytic components in the preparation of (co)polymers of olefins. For example, EP-A-185.918 describes the preparation of isotactic polypropylene in the presence of a catalytic system comprising alumoxane and ethylenebis(4,5,6,7-tetrahydro-1-indenyl) zirconium dichloride.

U.S. Pat. No. 5,268,495 describes a new method for the preparation of metallocenes bridge-linked to the cyclopentadienyl ring. According to this document the bridged metallocenes having as ligands derivatives of cyclopentadienyl have interesting properties and should be capable of (co)polymerizing a wide range of olefins.

New metallocenes have now been found, capable of (co)polymerizing $C_2$–$C_{20}$ olefins, particularly of copolymerizing ethylene with $C_3$–$C_{20}$, preferably $C_3$–$C_{10}$, even more preferably $C_3$ alpha-olefins, possibly in the presence of a diene.

The (co)polymers thus obtained can have a wide range of molecular weights, can be with or without elastomeric properties and can therefore be applied in various fields.

In accordance with this, the present invention relates to a catalytic component for the copolymerization of ethylene with $C_3$–$C_{20}$, preferably $C_3$–$C_{10}$, even more preferably $C_3$ alpha-olefins, possibly in the presence of a diene, having general formula (I):

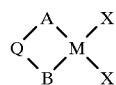

(I)

wherein:

A is a cyclopentadienyl derivative having general formula

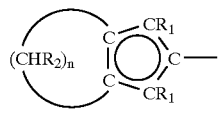

(II)

wherein $R_1$ and $R_2$ are selected from H and $C_1$–$C_3$, alkyl radicals, preferably $R_2$=H and at least one of the two $R_1$=H; n is an integer from 2 to 18, and is preferably selected from 3, 5, 6 and 10;

B is selected from:
1) any of the cyclopentadienyl derivatives A defined above;
2) a monofunctional cyclopentadienyl radical (F) selected from cyclopentadienyl, indenyl, fluorenyl and relative alkyl, aryl, trialkylsilyl substituted derivatives;

Q, a bridge between A and B, is a bifunctional radical selected from:
a) a $C_1$–$C_{20}$ alkylene group, linear, branched or cyclic;
b) a silanylene or disilanylene alkyl substituted group;
c) an alkyl substituted silaalkylene group;

M is selected from Titanium, Zirconium, Hafnium, Vanadium, Niobium, and is preferably Zirconium;

X is selected from halogen, hydrogen, $C_1$–$C_{10}$ alkyl group, $C_1$–$C_{10}$ alkoxide group, $C_2$–$C_{20}$ amide group, $C_2$–$C_{20}$ carboxyl group, $C_6$–$C_{10}$ aryl group, $C_6$–$C_{10}$ aryloxy group, $C_2$–$C_{10}$ alkenyl group, $C_7$–$C_{40}$ arylalkyl group, $C_7$–$C_{40}$ alkylaryl group, $C_8$–$C_{40}$ arylalkenyl group, preferably a $C_1$–$C_3$ alkyl group or a halogen, preferably chlorine.

The bridged ligands A—Q—B and their preparation are described in copending patent application filed by the same applicant as Italian patent application IT-A-MI 95/002284.

Some examples of compounds having general formula (I) are provided in FIG. (1).

In particular, belonging to compounds having general formula (I) and indicated in FIG. (1) are:

dimethylsilyl-bis(4,5,6,7,8-pentahydroazulen-2-yl)zirconium dichloride (CP136A, example Nr. 1.1 of FIG. 1);

[1-(3-methyl-Inden-1-yl)-1-methyl-ethyl-4,5,6,7,8-pentahydroazulen-2-yl]zirconium dichloride (CP172, example Nr. 1.2 of FIG. 1);

[1-(Inden-1-yl)-1-methyl-ethyl]-4,5,6,7,8-pentahydroazulen-2-ylzirconium dichloride (CP138E, example Nr. 1.3 of FIG. 1);

dimethylsilyl-bis-(4,5,6,7,8,9,10,11,12,13-decahydrocyclopentacyclododecen-2-yl)zirconiumdichloride (CP192, example Nr. 1.4 of FIG. 1);

1,2-bis-(4,5,6,7,8-pentahydroazulen-2-yl)-tetramethyldisilyl-zirconiumdichloride (CP191C, example Nr. 1.5 of FIG. 1);

1-[4,5,6,7,8-pentahydroazulen-2-yl]-2-[3-methyl-inden-1-yl]-tetramethyldisilylzirconiumdichloride (CP266E, example Nr. 1.6 of FIG. 1).

In one embodiment, Q is a linear, branched or cyclic alkylene group having from 1 to 20 carbon atoms. Typical examples are: methylene, ethylene, propylene, butylene, pentylene, hexylene, isopropylidene ($CH_3$—C—$CH_3$), isobutylidene ($CH_3$—C—$C_2H_5$), ($C_2H_5$—C—$C_2H_5$).

In another embodiment, Q is a silanylene or disilanylene alkyl substituted group, for example dimethylsilanylene, or —$Si(CH_3)_2$—, tetramethyl disilanylene, or —$Si(CH_3)_2$—Si$(CH_3)_2$—, methyl ethyl silanylene, diethylsilanylene.

In another embodiment, the Q group consists of Silicon-Carbon sequences, i.e. it is a sila-alkylene alkyl substituted group, for example —$Si(R')_2$—$C(R'')_2$—, wherein R' is a low alkyl and R'' is hydrogen or a low alkyl. Typical examples of sila-alkylene groups are:
1-sila-1,1-dimethylethylene;
2-sila-2,2-dimethylpropylene;
1,3-disila-1,1,3,3-tetramethylpropylene.

In the preferred embodiment Q is selected from branched alkylene and dialkylsilanylene derivatives, even more preferably it is selected from isopropylidene, dimethylsilanylene and tetramethyldisilanylene.

In the case that B is equal to any of the radicals (A) defined in general formula (II), in the product having general formula (I) the group Q forms a bridge with two cyclopentadienyl derivatives both linked to Q in position 2 of the cyclopentadienyl ring.

When B is a derivative (F) different from (A), it is a monofunctional cyclopentadienyl radical selected from cyclopentadienyl, indenyl, fluorenyl and the relative alkyl, aryl, trialkylsilyl substituted derivatives; in the preferred embodiment (F) is selected from cyclopentadienyl, indenyl and fluorenyl. For the sake of simplicity we shall call these compounds A—X—C.

In the case that B is selected from F radicals, the attachment point of the above derivatives to the bridge Q is well known to experts in the field. For example, indenyl will bind itself to Q from position 1, whereas fluorenyl will be bound to Q from the only non-condensed position of the ring with 5 chain-ends.

The present invention also relates to a process for the preparation of metallocenes having general formula (I) which comprises the reaction of a compound having the general formula HA—Q—BH (wherein Q, A and B have the meaning defined above) with a metalloalkyl, preferably a Lithium alkyl, to give the corresponding dianion, and subsequent reaction with $MX_4$, preferably with Zirconium tetrachloride, to give the compound having general formula (I). The reaction scheme, illustrated for Lithium butyl and $ZrCl_4$, is the following:

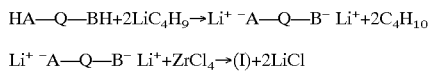

A further object of the present invention relates to a process for the homo and copolymerization of $C_2$–$C_{20}$ alpha-olefins, particularly for the copolymerization of ethylene with $C_3$–$C_{10}$ alpha-olefins, even more preferably with propylene, optionally in the presence of dienes, which use a catalytic system which comprises the compound having general formula (I).

In the (co)polymerization of alpha-olefins, the catalytic system comprises, apart from the metallocene having general formula (I), also another component (which we shall call cocatalyst) selected from alumoxane and compounds having general formula (III) $(Ra)_xNH_{4-x}B(Rd)_4$, or (IV) $(Ra)_3PHB(Rd)_4$, or (V) $B(Rd)_3$, or (VI) $CPh_3[B(Rd)_4]$, which by reaction with a metallocene having general formula (I) are capable of generating catalytic systems of an ionic nature. In the above compounds having general formula (III), (IV), (V) or (VI), the Ra groups, the same or different, are monofunctional alkyl or aryl radicals, whereas Rd, the same or different, are monofunctional aryl radicals, preferably partially or totally fluorinated, even more preferably totally fluorinated. When compounds having the general formula (III), (IV), (V) or (VI) are used, the catalytic system will essentially consist of reaction products of one or more metallocenes having general formula (I), with X equal to H or to a hydrocarbyl radical, with any of the compounds having general formula (III), (IV), (V) or (VI), or their mixture, as described in EP-A-277.004, the molar ratio between the compound having general formula (III), (IV), (V) or (VI) and the metallocene having general formula (I) being between 0.1 and 19, preferably from 0.5 to 6, even more preferably from 0.7 to 4.

When, in the compound having general formula (I), X is different from H or from a hydrocarbyl radical, the catalytic system will consist of one or more metallocenes having general formula (I), an alkylating compound (VII) selected from aluminum trialkyl, magnesium dialkyl or lithium alkyl or other alkylating agents well known to experts in the field, and any of the compounds having general formula (III), (IV), (V) or (VI), or their mixture.

The procedure for the formation of the catalytic system involves the premixing of the metallocene compound having general formula (I) with the appropriate alkylating agent (VII) in hydrocarbon solvents, aliphatic or aromatic or their mixtures, at a temperature of between −20° C. and +100° C., preferably from 0° C. to 60° C. and even more preferably from +20° C. to +50° C., for a time which varies from 1 minute to 24 hours, preferably from 2 minutes to 12 hours, even more preferably from 5 minutes to 2 hours. The mixture is then put in contact with a compound having general formula (III), (IV), (V) or (VI), at the above temperature for a time of between 1 minute and 2 hours, preferably between 2 minutes and 30 minutes, and is subsequently fed to the polymerization reactor.

The molar ratio between the alkylating compound (VII) and the compound having general formula (I) can vary from 1 to 1000, preferably from 10 to 500, even more preferably from 30 to 300.

The molar ratio between the compound having general formula (III), (IV), (V) or (VI) and the metallocene (I) can vary from 0.1 to 10, preferably from 0.5 to 6, even more preferably from 0.7 to 4.

With respect to the alumoxane, this is a compound of aluminum which, in its linear form, has the general formula (VIII)

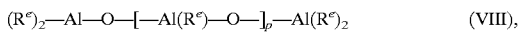

whereas in its cyclic form, it has the general formula $$(IX) \quad —[—O—Al(R^e)—]_{p+2}—$$

wherein the various $R^e$, the same or different, are selected from $C_1$–$C_6$ alkyl radicals, $C_6$–$C_{18}$ aryl radicals or H, "p" is an integer from 2 to 50, preferably from 10 to 35. The various $R^e$ are preferably equal and are selected from methyl, isobutyl, phenyl or benzyl, preferably methyl.

When the various $R^e$ are different, they are preferably methyl and hydrogen or alternatively methyl and isobutyl, the hydrogen or isobutyl being preferably present, as a number of $R^e$ radicals, in from 0.01 to 40% by weight.

The alumoxane can be prepared with the various methods known to experts in the field. One of the methods comprises, for example, the reaction of an aluminumtrialkyl compound and/or an aluminum dialkylmonohydride with water (gaseous, solid, liquid or bound, for example such as crystallization water) in an inert solvent, for example toluene. For the preparation of an alumoxane having different $R^e$ alkyl groups, two different aluminumtrialkyls ($AlR_3$+$AlR'_3$) are reacted with water (see S. Pasynkiewicz, Polyhedron 9 (1990) 429–430 and EP-a-302.424).

The exact structure of the alumoxane is not known.

It is possible to preactivate the metallocene with the alumoxane before its use in the polymerization phase. This considerably increases the polymerization activity. The above preactivation is preferably carried out in a solvent, by dissolving the metallocene in a solution of an inert hydrocarbon, preferably aliphatic or aromatic, even more preferably in toluene. The concentration of the alumoxane in the solution is within the range of 1% by weight up to the saturation value, preferably from 5 to 30% by weight, with respect to the total weight of the solution. The metallocene can be used in the same concentration but is preferably used in a quantity of from $10^{-4}$ to 1 mole per mole of alumoxane. The preactivation lasts from 5 minutes to 60 hours, preferably from 5 minutes to 60 minutes. The temperature is from −78° C. to 100° C., preferably from 0° to 70° C.

The catalytic system of the present invention (catalyst having general formula I and cocatalyst) can be prepared by putting the catalyst in contact with the cocatalyst in the presence of or without the monomer to be polymerized, inside or outside the reaction reactor.

The quantities of catalyst and cocatalyst are not particularly limited. For example, in the case of polymerization in slurry, the concentration of catalyst is preferably within the range of $10^{-8}$ to $10^{-1}$ moles/liter, even more preferably from $10^{-7}$ to $10^{-5}$ moles/liter, in terms of transition metal M. When alumoxane is used, the molar ratio between the Aluminum and the transition metal M is preferably greater than 10 and less than 10,000.

As well as the catalyst and cocatalyst, the catalytic system can contain a third optional component, usually one or more substances having active hydrogen atoms, such as water, alkanols (for example methanol, ethanol, butanol), or electron-donor compounds such as ethers, esters, amines, compounds containing alkoxy groups such as phenylborates, dimethylmethoxyaluminum, phenyl phosphate, tetraethoxysilane, diphenyldimethoxysilane.

The catalyst and cocatalyst can be introduced separately into the reaction reactor or after they have been put in previous contact with each other. In the latter case the contact can be carried out in the presence of a monomer which is then to be polymerized, thus effecting the so-called "pre-polymerization".

To come back to the copolymerization process, it is preferable to remove catalyst poisons possibly present in the monomers, particularly in propylene. In this case the purification can be carried out with an aluminumalkyl, for example $AlMe_3$, $AlEt_3$, $Al(iso-Bu)_3$. This purification can be carried out in the polymerization system itself or, alternatively, before polymerization by putting the monomers in contact with the Aluminum alkyl and subsequently separating them.

The catalytic system of the present invention can be applied to polymerization in slurry phase (where an inert medium is used as suspending agent, for example propane or butane, possibly propylene itself and relative mixtures), polymerization in gas phase and polymerization in solution. The catalyst of the invention can obviously be applied to polymerization in continuous or batch.

When the polymerization is carried out in solvent, aliphatic and aromatic hydrocarbons can be conveniently used as diluents, either alone or mixed with each other.

The catalytic component having general formula (I) can be supported on inert carriers. Suitable techniques are known in literature for supporting metallocene components on porous solids, for example silica and alumina, possibly in the presence of the cocatalyst. The catalytic system thus supported can be used as such or prepolymerized with alpha-olefinic monomers. Supporting allows heterogeneous catalytic components to be obtained with a morphology and specific particle size, which are particularly suitable for polymerization processes in gas phase.

The polymerization temperature is approximately within the range of $-78°$ C. to $200°$ C., preferably from $-20°$ C. to $100°$ C. There are no particular limitations to the pressure of olefin in the reaction system, even if the pressure preferably ranges from atmospheric pressure to 5 MPa.

In the polymerization process the molecular weight can be controlled with any known method, for example by suitably selecting the polymerization temperature and pressure, or introducing hydrogen.

The olefins which can be polymerized with the process of the present invention are alpha-olefins (including ethylene) having from 2 to 20 carbon atoms, preferably from 2 to 10 carbon atoms. Typical examples of alpha-olefins which can be (co)polymerized with the process of the present invention are ethylene, propylene, 1-butene, 4-methyl-1-pentene, 1-hexene, 1-octene, 1-decene, 1-dodecene, 1-tetradecene, 1-hexadecene, 1-octadecene, 1-eicosene.

Dienes which can possibly be copolymerized with the alpha-olefins, particularly with $C_2$–$C_3$ olefins, are elected, as is known to experts in the field, from:

dienes with a linear chain such as 1,4-hexadiene and 1,6-octadiene;

acyclic dienes with a branched chain such as 5-methyl-1,4-hexadiene; 3,7-dimethyl-1,6-octadiene; 3,7-dimethyl-1,7-octadiene; dihydro myrcene and dihydroocimene;

alicyclic dienes with a single ring such as 1,4-cyclohexadiene; 1,5-cyclooctadiene; 1,5-cyclododecadiene;

dienes having alicyclic bridge-linked rings such as methyltetrahydroindene; dicyclopentadiene; bicyclo-(2,2,1) hepta-2,5-diene; alkenyl, alkylidene, cycloalkenyl and cycloalkylidene norbornenes such as 5-methylene-2-norbornene (MNB); 5-ethylidene-2-norbornene (ENB); 5-propenyl-2-norbornene; 5-isopropenyl-2-norbornene; 5-cyclohexylidene-2-norbornene.

Among non-conjugated dienes typically used for preparing these copolymers, dienes containing at least one double bond in a strained ring are preferred. The third monomer which is most preferred is 5-ethylidene-2-norbornene (ENB).

When EPDM are prepared, the content of diene in the polymer is less than 15% by weight, preferably from 2 to 10%, the content of propylene being that indicated above.

More specifically a further object of the present invention relates to a process in slurry phase for the preparation of ethylene/α-olefin copolymers or ethylene/α-olefin/diene terpolymers, preferably ethylene-propylene (EPM) or ethylene-propylene-diene (EPDM) with a propylene content of between 10 and 75% by weight, preferably from 15 to 70% by weight, which comprises the following steps:

1) an α-olefin and the possible diene, optionally diluted with a hydrocarbon are fed into a polymerization reactor, at such a pressure as to allow the use of said α-olefin in liquefied form;
2) ethylene is added to the mixture obtained in step (1) in a sufficient quantity to maintain the desired ratio ethylene/α-olefin in liquid phase;
3) the catalytic system is added, comprising one or more metallocenes and one or more cocatalysts selected from alumoxane and compounds having general formula (III) $(Ra)_xNH_{4-x}B(Rd)_4$, or (IV) $(Ra)_3PHB(Rd)_4$, or (V) $B(Rd)_3$, or (VI) $CPh_3[B(Rd)_4]$, possibly in the presence of an alkylating compound (VII);
4) the mixture obtained in step (3) is reacted for a sufficient time to allow the polymerization of the ethylene/alpha-olefin system and possible diene, characterized in that the catalytic system comprises a metallocene selected from those having general formula (I)

(I)

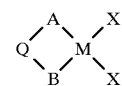

wherein:

A, B, Q, M, X have the meaning defined above.

When EPDM are prepared, the content of diene in the polymer is less than 15% by weight, preferably from 2 to 10%, the content of propylene being that indicated above.

The process for the production of EP(D)M is carried out by polymerization in slurry phase of ethylene and the alpha-olefin, preferably propylene, and the possible diene, optionally diluted with a hydrocarbon, preferably low-boiling $C_3$ to $C_5$, even more preferably with propane. In this mixture a catalytic system is suspended, consisting of the metallocene having general formula (I) and the cocatalyst selected from MAO and compounds having general formula (III) to (VI), and possibly the alkylating compound (VII). This catalytic system is present in such a quantity as to provide a sufficient quantity of polymer containing the possible diene.

The concentration of the possible diene in the reactor, as percentage by volume, is from 0.05 to 10%, preferably from 0.2 to 4%.

An embodiment of the present invention according to the process in slurry is described hereunder as an illustration.

Liquid propylene is fed in continuous into a stirred reactor together with the ethylene and possible diene, optionally diluted with a low-boiling $C_3$–$C_5$ hydrocarbon. The reactor contains a liquid phase essentially consisting of liquid propylene, possible diene monomers, an optional low-boiling hydrocarbon together with gaseous ethylene dissolved therein, and a gaseous phase containing vapors of all the components. The ethylene fed is introduced either as gas in the vapour phase of the reactor, or dispersed in the liquid phase, as is known to experts in the field.

The components of the catalytic system (catalyst, cocatalyst, optional alkylating compound and a possible scavenger) can be charged into the reactor through additional valves, either in gaseous or liquid phase, preferably in liquid phase.

The polymerization takes place in liquid phase generating a copolymer either soluble or insoluble in the phase itself, with a residence time of the suspension in the reactor varying from 10 minutes to 10 hours, preferably from 30 minutes to 2 hours; longer residence times give final polymers with a lower content of catalytic residues.

The temperature of the reactor can be controlled by cooling the reactor by means of a coil or jacket in which cooling liquid circulates or, more preferably, by evaporating and condensing the alpha-olefin (and the possible low-boiling hydrocarbon) and refeeding them inside the reactor.

The ethylene is fed to the reactor at a pressure higher than the pressure existing inside the reactor. The ethylene content of the polymer is determined by the ratio between the partial ethylene pressure and the total pressure in the polymerization reactor. This partial ethylene pressure is generally maintained at between 0.5 and 50 bars, more preferably between 1 and 15 bars. The temperature of the reactor is kept at between −10° C. and 90° C., more preferably between 20° C. and 60° C. With these operating conditions, ethylene, alpha-olefin and the possible diene polymerize to give an EP(D)M copolymer.

The final treatment of the reaction mixture depends on the molecular weight of the copolymer produced. In fact, the process of the present invention allows the production, depending on the operating conditions, more specifically depending on the metallocene used in the polymerization, of copolymers having different molecular weights which can therefore be used in various fields of application.

Copolymers with an $M_w$ value of up to $10^5$ can be used for example as bases for the production of additives for lubricating oils and for gas oil with dispersing characteristic and viscostaticity or both.

For higher $M_w$ values, corresponding to Mooney viscosity (ML1+4, 100) greater than 25, the copolymers and terpolymers of the present invention can be applied in the construction of vulcanized end-products such as tubes, seals, coating for electric cables and other technical items, using formulations known in the art containing, as cross-linking agents, peroxides (in the case of copolymers) or sulfur with accelerators (in the case of terpolymers).

The following examples are provided for a better understanding of the present invention.

EXAMPLE 1

Synthesis of dimethylsilyl-bis-(4,5,6,7,8-pentahydroazulen-2-yl)zirconiumdichloride (CP136A)

8.5 ml (0.0136 moles) of LiMe 1.6 M in ethyl ether are added, at room temperature, to the solution of 2.2 g (0.0068 moles) of bis-(2,4,5,6,7,8-hexahydroazulen-2-yl) dimethylsilane, prepared as described in example 1 of Italian patent application IT-A-MI 95/002284, dissolved in 100 ml of ethyl ether. The mixture is left under stirring for 4 hours, is then cooled to −70° C. and 1.8 g (0.0077 moles) of $ZrCl_4$ are added. The temperature is left to rise to room temperature, the stirring being maintained for a further 2 hours, the mixture is then filtered, washed with ethyl ether and then hexane. It is extracted with methylene chloride, concentrated and filtered. The solid is washed with a small amount of methylene chloride then with hexane and is finally dried obtaining 0.4 g of complex (12% yield of the ligand used).

$^1$H NMR ($CDCl_3$, δ ppm rel. TMS): 5.38 (s, 4H); 2.8 (m, 8H); 2.0 (m, 8H); 1.65 (m, 4H); 0.81 (s, 6H).

$^{13}$C NMR ($CDCl_3$, δ rel. TMS): −4.49; 29.26; 31.30; 32.60; 101.60; 115.50; 143.16.

EXAMPLE 2

Synthesis of [1-(3-methyl-Inden-1-yl)-1-methyl-ethyl]-4,5,6,7,8-pentahydroazulen-2-yl zirconiumchloride (CP172)

0.3 g of t-BuOK are added to a mixture of 4.5 g (0.0336 moles) of 2,4,5,6,7,8-hexahydroazulene, prepared according to example 1 of Italian patent application A-MI 95/002707, 70 ml of MeOH and 10 ml of acetone and maintained at reflux for 20 hours. A further 2.7 g of t-BuOK are then added and reflux is maintained for another 25 hours. At the end the mixture is poured into water and is extracted with ethyl ether. The ether extract after neutralization and anhydrification is evaporated and the residue is purified by elution on a silica gel column using petroleum ether. 3.8 g of fulvene derivative 2-isopropylidene-2,4,5,6,7,8-hexahydroazulene are obtained as a yellow solid (65% yield).

12.4 ml of LiBu 2.5 M in hexane are added, at room temperature, to an ether solution of 4.2 g (0.032 moles) of 1-methylindene in 100 ml of ethyl ether. The mixture is left under stirring for 3 hours, then 3.8 g (0.022 moles) of 2-isopropylidene-2,4,5,6,7,8-hexahydroazulene are added at −70° C. The temperature is left to rise and the mixture is left under stirring for 48 hours. The reaction mixture is hydrolyzed in water and extracted with ethyl ether which after evaporation provides a solid which is purified on a silica gel column using petroleum ether as eluant. 4.5 g (0.0148 moles) of 2-[1-(3-methyl-1H-Inden-1-yl) -1-methyl-ethyl]-1,4,5,6,7,8-hexahydroazulene are obtained which are dissolved in 200 ml of ethyl ether, to which 18.8 ml of LiMe 1.6 M in ether ethyl are added and the mixture is left under stirring for a night. A slightly yellow precipitate is formed. The mixture is cooled to −70° C. and 3.51 g (0.015 moles) of zirconium tetrachloride are added. The temperature is brought to room temperature and the mass tends to take on a dark brownish-yellow coloring. The mixture is filtered, washed with ethyl ether which tends to become yellow, and is then extracted with methylene chloride (2×100 ml). The solution is brought to a small volume and 20 ml of ethyl ether are then added. A solid precipitates which is filtered, washed with ether and hexane and then dried. 1.0 g of complex are obtained. After two days large orange crystals separate from the yellow ether mother liquor, which when filtered and washed with hexane give 2.1 g of pure complex for a total of 3.1 g (45% yield calculated on the ligand used).
$^1$H NMR (CDCl$_3$, δ ppm rel. TMS): 7.55 (d, 2H); 7.25 (m, 1H); 6.95 (m, 1H); 5.65 (s, 1H); 5.43 (d, 1H); 2.8–2.5 (m, 4H); 2.45 (s, 3H); 1.9–1.6 (m, 7H); 1.40 (m, 2H).

EXAMPLE 3

Synthesis of
[1-(Inden-1-yl)-1-methyl-ethyl]-4,5,6,7,8-pentahydroazulen-2-ylzirconiumdichloride (CP138E)

3.5 g (0.0121 moles) of 2-[1-(1H-Inden-1-yl)-1-methylethyl]-1,4,5,6,7,8-hexahydroazulene are prepared, according to what is described in example 2 of Italian patent application IT-A-MI 95/A 002284, which are dissolved in 200 ml of ether and 15.2 ml of a 1.6 M solution in ether of LiMe are added, at room temperature. At the end of the addition the mixture is left under stirring for a night. A slightly yellow precipitate is formed. The mixture is cooled to –70° C. and 2.83 g (0.0121 moles) of solid zirconium tetrachloride are added. The temperature is brought to room temperature and the mass tends to take on a dark brownish-yellow coloring. The mixture is filtered, washed with ethyl ether which tends to become yellow, and is then extracted with methylene chloride (2×100 ml). The solution is brought to a small volume and 20 ml of ethyl ether are then added. A solid precipitates which is filtered, washed with ether and hexane and then dried. 0.8 g of complex are obtained. After two days large orange crystals separate from the yellow ether mother liquor, which when filtered and washed with hexane give 1.6 g of pure complex for a total of 2.4 g (0.0053 moles, 44% yield).
$^1$H NMR (CDCl$_3$, δ ppm rel. TMS): 7.59 (m, 2H); 7.30 (m, 1H); 7.05 (m, 1H); 6.90 (d, 1H); 6.00 (d, 1H); 5.42 (d, 1H); 5.25 (d, 1H); 2.60 (m, 4H); 2.15 (s, 3H); 1.86 (s, 3H); 1.80 (m, 4H); 1.40 (m, 2H).

EXAMPLE 4

Synthesis of dimethylsilyl-bis-(4,5,6,7,8,9,10,11,12,13-decahydrocyclopentacyclododecen-2-yl)zirconiumdichloride (CP192)

2.2 g (0.0047 moles) of bis-(4,5,6,7,8,9,10,11,12,13-decahydro- 2H-cyclopentacylododecen-2-yl) dimethylsilane, prepared as described in example 3 of Italian patent application IT-A-MI 95/002707, are dissolved in 50 ml of ethyl ether and 5.9 ml of LiMe 1.6 M in ether are added. The mixture is stirred for 1.5 hours, cooled to –70° C. and 1.1 g (0.0047 moles) of solid ZrCl$_4$ are added. The suspension is left to return to room temperature, is stirred for a further 2 hours, filtered and extracted with methylene chloride. The solution is concentrated and the solid which precipitates is filtered, washed with a small amount of ether then with hexane and is finally dried obtaining 0.66 g (0.0011 moles) of complex with a yield of 23% of the zirconium chloride used.
$^1$H NMR (CDCl$_3$, δ ppm rel. TMS): 5.51 (s, 4H); 2.59 (t, 8H); 1.6 (m, 8H); 1.30 (m, 24H); 0.63 (s, 6H).
$^{13}$C NMR (CDCl$_3$, δ rel. TMS): –5.01; 22.84; 25.12; 25.14; 25.94; 29.50; 114.18; 141.07.

EXAMPLE 5

Synthesis of 1,2-bis-(4,5,6,7,8-pentahydroazulen-2-yl)-tetramethyldisilylzirconiumdichloride (CP191C)

A suspension of 5.1 g (0.036 moles) of lithium salt of 2,4,5,6,7,8-hexahydroazulene, prepared as described in Italian patent application IT-A-MI 95/002731, is cooled to –70° C. and 3.4 g (0.018 moles) of 1,2-dichlorotetramethyldisilane are added dropwise. The temperature is left to rise to room temperature during the night. The reaction mixture is hydrolyzed and extracted with petroleum ether. On evaporation of the solvent, 6.5 g of solid product are obtained which, after grinding in methanol, give 4.6 g (0.012 moles, 67% yield) of pure 1,2-bis-(2,4,5,6,7,8-hexahydroazulen-2-yl)-tetramethyldisilane. The ligand is dissolved in 160 ml of ethyl ether and 15 ml of LiMe 1.6 M in ethyl ether are added. A solid with a rubbery appearance separates. 50 ml of THF are then added in which the solid dissolves subsequently forming a white crystalline precipitate. The mixture is stirred for an hour and cooled to –70° C. 3.2 g (0.0137 moles) of ZrCl$_4$ are then added and the temperature is left to rise to room temperature. The mixture is filtered and the white solid is washed with ethyl ether and then with hexane. The residue is extracted with methylene chloride (3×50 ml). The volume is reduced to 20 ml and the solid obtained is filtered and washed with a small amount of methylene chloride. 0.82 g of complex are obtained (13% yield).
$^1$H NMR (δ ppm rel. to TMS): 6.29 (s, 4H); 2.8 (dt, 4H); 2.55 (dd, 4H); 2.05 (m, 2H); 1.90 (m, 4H); 1.55 (q, 2H); 1.18 (q, 4H); 0.40 (s, 12H).
$^{13}$C NMR (δ ppm rel. to TMS): –2.3; 28; 30; 32; 116; 124; 138.5.

EXAMPLE 6

Synthesis of 1-[4,5,6,7,8-pentahydroazulen-2-yl]-2-[3-methyl-inden-1-yl]-tetramethyldisilylylzirconiumdichloride. (CP266E)

5.1 g (0.036 moles) of lithium salt of 2,4,5,6,7,8-hexahydroazulene, prepared as in example 5, are dissolved in 200 ml of THF and maintained at –70° C. 9.0 g (0.048 moles) of 1,2-dichloro-tetramethyldisilane are added dropwise. The temperature is left to rise to room temperature and the solvent is then evaporated. The residue is dissolved in pentane and filtered. The pentane is evaporated and the solid is dissolved in 75 ml of THF and added, at –70 ° C., to a solution of Lithium-1-methyl-indenyl prepared from 8.5 g (0.065 moles) of 1-methylindene in 150 ml of THF and 25 ml of LiBu 2.5 M in hexane. The temperature is left to return to room temperature, the mixture is hydrolyzed with water and extracted with petroleum ether. After evaporation of the solvent the residue is purified by elution on a silica gel column subsequently using petroleum ether and then petroleum ether containing 5% of methylene chloride. 10.4 g are thus obtained.

3.1 g (0.0082 moles) of the ligand previously prepared are dissolved in 150 ml of ethyl ether and 6.5 ml of LiBu 2.5 M in hexane are added. There is an immediate reaction with the formation of a precipitate. The mixture is left under stirring for 8 hours, is then cooled to –60° C. and 2.1 g (0.009 moles) of solid ZrCl$_4$ are added. The temperature is left to rise to room temperature and the mixture is then left under stirring for three hours. The suspension is then filtered and the filtrate concentrated to 15 ml. The solid obtained is then filtered and washed twice with a small amount of ethyl ether and then with pentane. After drying 1.3 g of complex are obtained (29% yield).
$^1$H NMR (δ ppm rel. to TMS): 7.74 (dd, 1H); 7.62 (dd, 1H); 7.26 (m, 2H); 6.68 (s, 1H); 6.38 (d, 1H); 5.78 (d, 1H); 2.66 (m, 4H); 2.50 (s, 3H); 1.88 (m, 4H); 1.40 (m, 2H); 0.59 (s, 3H); 0.52 (s, 3H); 0.48 (s, 3H); 0.47 (s, 3H).

POLYMERIC TESTS 1–16

Synthesis of ethylene/propylene copolymers and ethylene/propylene/diene terpolymers.

The polymerizations were carried out in a 3.3 liter pressure-resistant reactor, thermostat-regulated and equipped with a magnetic drag stirrer, according to the following procedure:

After flushing the reactor with propylene containing Aluminum triisobutyl at 5% by weight/volume and washing with fresh propylene, 2 liters of liquid propylene "polymerization grade" and possibly the third monomer (ENB) are fed at 23° C. The reactor is then brought to the preset temperature for the polymerization and a hexane solution at 10% of TIBA (triisobutyl aluminum) corresponding to 1.5 mmoles of Al, is introduced. The opotional hydrogen and ethylene in gaseous form are then added with a plunged pipe in the preset ratio in order to reach the partial pressures desired.

The catalyst is prepared as follows:

A solution of metallocene in 10 ml of anhydrous toluene is prepared in a glass funnel maintained in a nitrogen atmosphere, to which a solution of methylaluminoxane (MAO) at 30% in toluene is added (commercial product WITCO called Eurocen Al 5100/30T) in the quantity necessary for obtaining the desired ratio Al/Zr.

The resulting solution is poured into a steel barrel maintained in a nitrogen atmosphere and introduced rapidly into the reactor by means of a nitrogen overpressure. The pressure of the reactor is kept constant by feeding ethylene from a weight-controlled cylinder. After an hour, the feeding of the ethylene is interrupted, the residual monomers are degassed and the reactor is cooled to room temperature.

The polymer is discharged and homogenized with a roll mixer and finally characterized.

Table 1 indicates: C2=content of ethylene in the liquid phase (% moles); ENB=content of ENB in the liquid phase (% moles); T=temperature in ° C., H2=quantity of hydrogen (molecular weight regulator) fed into the reactor before the polymerization expressed in moles/liter; MAO/Zr=molar ratio between cocatalyst and Zr; Yield=polymerization yield (kg of polymer produced/g of Zr fed per hour of production); C3=content of propylene in the polymer produced (weight %); ENB=content of ENB in the polymer produced (weight %);=intrinsic viscosity of the polymer in dl/g; Mooney= Mooney viscosity ML (1+4, 100° C.); Mw=weight average molecular weight; Mw/Mn=ratio between weight average molecular weight and number average molecular weight.

POLYMERIC TEST 17

Unlike the previous examples, this test was carried out using a catalytic system prepared according to the ion couple technique.

2 ml of toluene, 0.3 mg ($5.53 \times 10^{-7}$ moles) of metallocene CP 191C, prepared according to what is described in example 5, and a hexane solution at 10% of Al(iso-Bu)$_3$ so that the molar ratio Al/Zr is equal to 300, were introduced into a 100 ml glass test-tube, pumped with nitrogen.

The solution is thermostat-regulated for 1 hour at 20° C. under stirring, then diluted with 1 ml of toluene and a solution at 0.2% in toluene of $(C_6H_5)_3C[B(C_6F_5)_4]$ is added so that the molar ratio B/Zr is equal to 4.

The solution obtained is then immediately fed into a pressure-resistant reactor previously fed with 2 liters of propylene and $0.9 \times 10^{-3}$ moles of Al(i-Bu)$_3$, thermostat-regulated at 45° C. and saturated with ethylene to have an ethylene content of 20% molar in the liquid phase.

After an hour of polymerization 270 g of copolymer were discharged having a content of propylene of 39% by eight and a Mooney viscosity ML (1+4, 100° C.) of 23.

The polymerization yield was equal to 5400 kilograms per gram of zirconium per hour.

This example shows that the catalysts of the present invention provide ethylene/propylene copolymers with a high productivity using, as an alternative cocatalyst to MAO, an activator capable of generating an ionic couple by reaction with the metallocenes having general formula (I).

Physico-chemical Analyses and Characterizations

The following measurements are carried out on the polymers obtained:

Propylene content and ENB content:

The determination is carried out via IR on the polymers in the form of film with a thickness of 0.2 mm, using an FTIR Perkin-Elmer spectrophotometer model 1760.

Intrinsic Viscosity:

The measurements are carried out at 135° C. with the polymer dissolved in orthodichlorobenzene. The fall times of the solvent and solutions are measured with an Ubbelhode type viscometer at increasing concentrations in the polymer under examination.

The extrapolation of the viscosities reduced and relating to concentration zero provides the intrinsic viscosity value.

Molecular weight distribution:

The analysis is carried out with gel permeation chromatography in orthodichlorobenzene at 135° C. using a Waters ALC/GPC 135 instrument. The calibration curve used for the calculation of the molecular weight is obtained with mondispersed standard samples of polystyrene, using the Mark-Houwink equation valid for linear polyethylene and polypropylene. The molecular weights are corrected in relation to the composition by means of the Sholte equation (J. Appl. Polym. Sci. 1984, 29, pages 3363–3782).

Mooney Viscosity (1+4)

This is determined at 100° C. using a Monsanto "1500 S" viscometer, according to the method ASTM D 1646/68.

TEST 18

Vulcanization

The mixture to be vulcanized was prepared using the following formulation (quantity referring to 100 parts of EPDM deriving from test 15): Carbon black 55 parts; zinc oxide 5 parts; Peroxide 5 parts; Sulfur 1.5 parts; Accelerators 2.25; Paraffinic oil 30 parts.

The mixture is vulcanized in a plate press at 165° C. for 40 minutes at 18 MPa.

The mechanical characteristics were carried out on vulcanized test samples taken from molded sheets.

The ultimate tensile strength (method ASTM D 412-68) proved to be=101 kg/cm$^2$, Elongation to break (ASTM D 412-68)=925%, Tension set at 200% (ASTM D 412-68)=12, Shore A=54.

TABLE 1

| Method | Test | C2 % | ENB % | T (° C.) | H2 | MAO/Zr (mol.) | Yield | C3 % | ENB % | η dl/g | Mooney | Mw /1000 | Mw/Mn |
|---|---|---|---|---|---|---|---|---|---|---|---|---|---|
| CP 172 | 1 | 20 | — | 40 | — | 4200 | 3600 | 38 | — | — | — | 3 | 2.7 |
| CP 172 | 2 | 20 | 0.4 | 40 | — | 3800 | 2550 | 38 | 3.7 | — | — | 5 | 2.4 |
| CP 138 | 3 | 20 | — | 40 | — | 3000 | 1740 | 54 | — | — | — | 2.5 | 2.5 |
| CP 266 E | 4 | 20 | — | 45 | — | 5000 | 1800 | 32 | — | — | >120 | | |
| CP 266 E | 5 | 10 | — | 45 | — | 4200 | 1300 | 49 | — | — | 100 | 244 | 2.5 |
| CP 266 E | 6 | 12 | — | 45 | 0.45 | 2500 | 900 | 49 | — | — | 68 | 198 | 2.4 |
| CP 266 E | 7 | 14 | 0.5 | 45 | 0.45 | 2600 | 610 | 43 | 0.5 | — | 53 | | |
| CP 266 E | 8 | 14 | 1 | 45 | 0.45 | 2000 | 500 | 43 | 1.5 | — | 56 | | |
| CP 136 A | 9 | 3 | — | 40 | — | 1170 | 100 | 37 | — | 0.45 | — | — | — |
| CP 136 A | 10 | 4.5 | — | 40 | — | 940 | 250 | 23 | — | 0.7 | — | 46 | 2.2 |
| CP 136 A | 11 | 8 | — | 40 | — | 2300 | 240 | 17 | — | 0.8 | — | — | — |
| CP 191 C | 12 | 16 | — | 40 | 0.45 | 4040 | 2000 | 48 | — | 1.7 | 66 | 197 | 2.3 |
| CP 191 C | 13 | 20 | — | 45 | 0.45 | 4900 | 4600 | 54 | — | 1.6 | 76 | — | — |
| CP 191 C | 14 | 18 | 0.4 | 40 | 0.45 | 4800 | 2570 | 45 | 1.3 | 1.9 | 90 | — | — |
| CP 191 C | 15 | 18 | 1 | 40 | 0.45 | 4800 | 2580 | 55 | 2.1 | 1.8 | 79 | 251 | 2.6 |
| CP 192 | 16 | 15 | — | 40 | — | 5050 | 300 | 38 | — | 0.47 | — | 26.5 | 1.9 |

With the metallocenes CP172 (tests 1 and 2), CP138E (test 3), CP136A (tests 9–11) and CP192 (test 16), copolymers are obtained with a low molecular weight suitable for the preparation of additives for lubricating oils; in particular the metallocene CP192 allows particularly narrow molecular weight distributions to be obtained (test 16), whereas the metallocene CP172 is characterized by high catalytic activities. Test 2 shows that with the same metallocene CP172 terpolymers with a low molecular weight containing ENB, can be obtained.

With the metallocenes CP191C and CP266E copolymers and terpolymers with a high molecular weight are obtained, particularly suitable for the preparation of vulcanized elastomers, as is also shown by the data obtained from the mechanical characterization after vulcanization of the polymer obtained from test 15.

We claim:

1. A catalytic component having general formula (I):

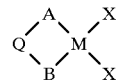
(I)

wherein:

A is a cyclopentadienyl derivative having general formula (II)

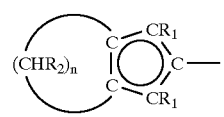
(II)

wherein $R_1$ and $R_2$ are selected from the group consisting of H and $C_1$–$C_3$ alkyl radicals; n is an integer from 2 to 18; B is selected from the group consisting of:
1) any of the cyclopentadienyl derivatives A defined above;
2) a monofunctional cyclopentadienyl radical (F) selected from the group consisting of cyclopentadienyl, indenyl, fluorenyl and alkyl, aryl, or trialkylsilyl substituted derivatives;

Q, a bridge between A and B, is a bifunctional radical selected from the group consisting of:

a) a $C_1$–$C_{20}$ alkylene group, linear, branched or cyclic;
b) a silanylene or disilanylene alkyl substituted group; and
c) a silaalkylene alkyl substituted group;

M is selected from the group consisting of zirconium, hafnium, vanadium and niobium;

X is selected from the group consisting of halogen, hydrogen, $C_1$–$C_{10}$ alkyl group, $C_1$–$C_{10}$ alkoxide group, $C_2$–$C_{20}$ amide group, $C_2$–$C_{20}$ carboxyl group, $C_6$–$C_{10}$ aryl group, $C_6$–$C_{10}$ aryloxy group, $C_2$–$C_{10}$ alkenyl group, $C_7$–$C_{40}$ arylalkyl group, $C_7$–$C_{40}$ alkylaryl group, $C_8$–$C_{40}$ arylalkenyl group.

2. The catalytic component according to claim 1, wherein M is Zirconium.

3. The catalytic component according to claim 1, wherein n is selected from 3, 5, 6 and 10.

4. The catalytic component according to claim 1, wherein X is selected from halogen, hydrogen, and hydrocarbyl radical.

5. The catalytic component according to claim 4, wherein the halogen is chlorine.

6. The catalytic component according to claim 1 wherein Q is selected from branched alkylene, dialkylsilanylenes and tetraalkylsubstituted disilanylens.

7. The catalytic component according to claim 6, wherein Q is selected from isopropylidene, dimethylsilanylene and tetramethyldisilanylene.

8. The catalytic component according to claim 1, wherein when group B is different from group A, group B is selected from cyclopentadienyl, indenyl and fluorenyl.

9. The catalytic component according to claim 1, wherein $R_2$=H and at least one of the two $R_1$=H.

10. A process for the preparation of the catalytic component having general formula (I):

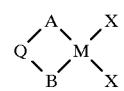
(I)

wherein:

A is a cyclopentadienyl derivative having general formula (II)

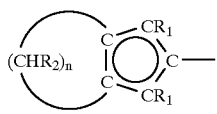

wherein $R_1$ and $R_2$ are selected from the group consisting of H and $C_1$–$C_3$ alkyl radicals; n is an integer from 2 to 18; B is selected from the group consisting of:
1) any of the cyclopentadienyl derivatives A defined above;
2) a monofunctional cyclopentadienyl radical (F) selected from the group consisting of cyclopentadienyl, indenyl, fluorenyl and alkyl, aryl, or trialkylsilyl substituted derivatives;

Q, a bridge between A and B, is a bifunctional radical selected from the group consisting of:
a) a $C_1$–$C_{20}$ alkylene group, linear, branched or cyclic;
b) a silanylene or disilanylene alkyl substituted group; and
c) a silaalkylene alkyl substituted group;

M is selected from the group consisting of titanium, zirconium, hafnium, vanadium and niobium;

X is selected from the group consisting of halogen, hydrogen, $C_1$–$C_{10}$ alkyl group, $C_1$–$C_{10}$ alkoxide group, $C_2$–$C_{20}$ amide group, $C_2$–$C_{20}$ carboxyl group, $C_6$–$C_{10}$ aryl group, $C_6$–$C_{10}$ aryloxy group, $C_2$–$C_{10}$ alkenyl group, $C_7$–$C_{40}$ arylalkyl group, $C_7$–$C_{40}$ alkylaryl group, $C_8$–$C_{40}$ arylalkenyl group, which comprises reacting a compound having general formula HA—Q—BH, wherein Q, A and B have the meaning defined above, with a metallocene to give the corresponding dianion, and subsequently reacting with $MX_4$, wherein X has the meaning defined above, to give the compound having general formula (I).

11. The process according to claim 10 wherein M=Zr, and wherein the metallocene is a Lithium alkyl and the compound $MX_4$ is Zirconium tetrachloride.

12. A process for the homo and copolymerization of $C_2$–$C_{20}$ alpha-olefin(s), optionally with diene(s), which comprises polymerizing said alpha-olefin(s), optionally with diene(s), in the presence of a catalyst comprising the catalytic component having general formula (I):

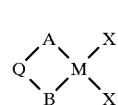

wherein:
A is a cyclopentadienyl derivative having general formula (II)

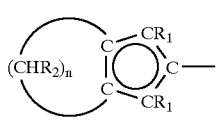

wherein $R_1$ and $R_2$ are selected from the group consisting of H and $C_1$–$C_3$ alkyl radicals; n is an integer from 2 to 18; B is selected from the group consisting of:

1) any of the cyclopentadienyl derivatives A defined above;
2) a monofunctional cyclopentadienyl radical (F) selected from the group consisting of cyclopentadienyl, indenyl, fluorenyl and alkyl, aryl, or trialkylsilyl substituted derivatives;

Q, a bridge between A and B, is a bifunctional radical selected from the group consisting of:
a) a $C_1$–$C_{20}$ alkylene group, linear, branched or cyclic;
b) a silanylene or disilanylene alkyl substituted group; and
c) a silaalkylene alkyl substituted group;

M is selected from the group consisting of titanium, zirconium, hafnium, vanadium and niobium;

X is selected from the group consisting of halogen, hydrogen, $C_1$–$C_{10}$ alkyl group, $C_1$–$C_{10}$ alkoxide group, $C_2$–$C_{20}$ amide group, $C_2$–$C_{20}$ carboxyl group, $C_6$–$C_{10}$ aryl group, $C_6$–$C_{10}$ aryloxy group, $C_2$–$C_{10}$ alkenyl group, $C_7$–$C_{40}$ arylalkyl group, $C_7$–$C_{40}$ alkylaryl group, $C_8$–$C_{40}$ arylalkenyl group.

13. A slurry process for the preparation of ethylene/α-olefin copolymers or ethylene/α-olefin/diene terpolymers, which comprises the following:

(1) feeding an α-olefin and optionally a diene, optionally diluted with a hydrocarbon, into a polymerization reactor, at such a pressure as to allow the use of said α-olefin in liquefied form;

(2) adding ethylene to the mixture obtained in (1) in a sufficient quantity to maintain a desired ratio of ethylene/α-olefin in liquid phase;

(3) adding a catalyst comprising one or more metallocenes and one or more cocatalysts selected from the group consisting of alumoxane and compounds having general formulae (III) $(Ra)_xNH_{4-x}B(Rd)_4$; (IV) $(Ra)_3PHB(Rd)_4$; (V) $B(Rd)_3$; and (VI) $CPh_3$, optionally in the presence of an alkylating compound, wherein the Ra groups are the same or different and are monofunctional alkyl or aryl radicals, and wherein the Rd groups are the same or different and are monofunctional aryl radicals, which are optionally partially or totally fluorinated;

(4) reacting the mixture obtained in (3) for a sufficient time to allow the polymerization of the ethylene and alpha-olefin, and optionally diene, wherein at least one of said metallocenes is the catalytic component having general formula (I):

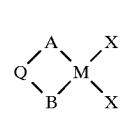

wherein:
A is a cyclopentadienyl derivative having general formula (II)

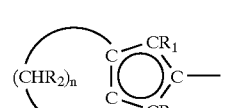

wherein $R_1$ and $R_2$ are selected from the group consisting of H and $C_1$–$C_3$ alkyl radicals; n is an integer from 2 to 18; B is selected from the group consisting of:
1) any of the cyclopentadienyl derivatives A defined above;
2) a monofunctional cyclopentadienyl radical (F) selected from the group consisting of cyclopentadienyl, indenyl, fluorenyl and alkyl, aryl, or trialkylsilyl substituted derivatives;

Q, a bridge between A and B, is a bifunctional radical selected from the group consisting of:
a) a $C_1$–$C_{20}$ alkylene group, linear, branched or cyclic;
b) a silanylene or disilanylene alkyl substituted group; and
c) a silaalkylene alkyl substituted group;

M is selected from the group consisting of titanium, zirconium, hafnium, vanadium and niobium;

X is selected from the group consisting of halogen, hydrogen, $C_1$–$C_{10}$ alkyl group, $C_1$–$C_{10}$ alkoxide group, $C_2$–$C_{20}$ amide group, $C_2$–$C_{20}$ carboxyl group, $C_6$–$C_{10}$ aryl group, $C_6$–$C_{10}$ aryloxy group, $C_2$–$C_{10}$ alkenyl group, $C_7$–$C_{40}$ arylalkyl group, $C_7$–$C_{40}$ alkylaryl group, $C_8$–$C_{40}$ arylalkenyl group.

14. The process of claim 12, wherein the $C_2$–$C_{20}$ alpha-olefins comprise a mixture of ethylene and $C_3$–$C_{10}$ alpha-olefins, optionally in the presence of dienes.

15. The process of claim 14, wherein the $C_3$–$C_{10}$ alpha-olefin is propylene.

16. The process of claim 13, wherein the ethylene/α-olefin copolymer is ethylene propylene (EPM) and the ethylene/α-olefin/diene terpolymer is ethylene-propylene-diene (EPDM) with a propylene content of from 10 to 75% by weight.

17. The process according to claim 16, wherein ethylene-propylene (EPM) or ethylene-propylene-diene (EPDM) copolymers are prepared with a propylene content of between 15 and 70% by weight.

18. A catalytic component having general formula (I):

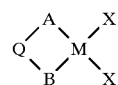

(I)

wherein:
A is a cyclopentadienyl derivative having general formula (II)

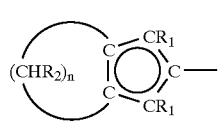

(II)

wherein $R_1$ and $R_2$ are selected from the group consisting of H and $C_1$–$C_3$ alkyl radicals; n is an integer from 2 to 3 or 5 to 18; B is selected from the group consisting of:
1) any of the cyclopentadienyl derivatives A defined above;
2) a monofunctional cyclopentadienyl radical (F) selected from the group consisting of cyclopentadienyl, indenyl, fluorenyl and alkyl, aryl, or trialkylsilyl substituted derivatives;

Q, a bridge between A and B, is a bifunctional radical selected from the group consisting of:
a) a $C_1$–$C_{20}$ alkylene group, linear, branched or cyclic;
b) a silanylene or disilanylene alkyl substituted group; and
c) a silaalkylene alkyl substituted group;

M is selected from the group consisting of titanium, zirconium, hafnium, vanadium and niobium;

X is selected from the group consisting of halogen, hydrogen, $C_1$–$C_{10}$ alkyl group, $C_1$–$C_{10}$ alkoxide group, $C_2$–$C_{20}$ amide group, $C_2$–$C_{20}$ carboxyl group, $C_6$–$C_{10}$ aryl group, $C_6$–$C_{10}$ aryloxy group, $C_2$–$C_{10}$ alkenyl group, $C_7$–$C_{40}$ arylalkyl group, $C_7$–$C_{40}$ alkylaryl group, $C_8$–$C_{40}$ arylalkenyl group.

19. A catalytic component having general formula (I):

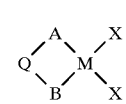

(I)

wherein:
A is a cyclopentadienyl derivative having general formula (II)

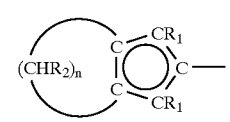

(II)

wherein $R_1$ and $R_2$ are selected from the group consisting of H and $C_1$–$C_3$ alkyl radicals; n is an integer from 2 to 18; B is selected from the group consisting of:
1) any of the cyclopentadienyl derivatives A defined above;
2) a monofunctional cyclopentadienyl radical (F) selected from the group consisting of cyclopentadienyl, indenyl, fluorenyl and alkyl, aryl, or trialkylsilyl substituted derivatives;

Q, a bridge between A and B, is a bifunctional radical selected from the group consisting of:
a) a $C_1$ or $C_3$–$C_{20}$ alkylene group, linear, branched or cyclic;
b) a silanylene or disilanylene alkyl substituted group; and
c) a silaalkylene alkyl substituted group;

M is selected from the group consisting of titanium, zirconium, hafnium, vanadium and niobium;

X is selected from the group consisting of halogen, hydrogen, $C_1$–$C_{10}$ alkyl group, $C_1$–$C_{10}$ alkoxide group, $C_2$–$C_{20}$ amide group, $C_2$–$C_{20}$ carboxyl group, $C_6$–$C_{10}$ aryl group, $C_6$–$C_{10}$ aryloxy group, $C_2$–$C_{10}$ alkenyl group, $C_7$–$C_{40}$ arylalkyl group, $C_7$–$C_{40}$ alkylaryl group, $C_8$–$C_{40}$ arylalkenyl group.

20. A catalytic component having general formula (I):

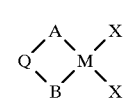

(I)

wherein:
A is a cyclopentadienyl derivative having general formula (II)

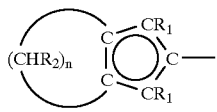

(II)

wherein $R_1$ and $R_2$ are selected from the group consisting of H and $C_1$–$C_3$ alkyl radicals; n is an integer from 2 to 18; B is selected from the group consisting of:
1) any of the cyclopentadienyl derivatives A defined above;
2) a monofunctional cyclopentadienyl radical (F) selected from the group consisting of cyclopentadienyl, indenyl, fluorenyl and alkyl, aryl, or trialkylsilyl substituted derivatives;

Q, a bridge between A and B, is a bifunctional radical selected from the group consisting of:
a) a $C_1$–$C_{20}$ alkylene group, linear, branched or cyclic;
b) a silanylene or disilanylene alkyl substituted group; and
c) a silaalkylene alkyl substituted group;

M is selected from the group consisting of titanium, zirconium, hafnium, vanadium and niobium;

X is selected from the group consisting of hydrogen, $C_1$–$C_{10}$ alkyl group, $C_1$–$C_{10}$ alkoxide group, $C_2$–$C_{20}$ amide group, $C_2$–$C_{20}$ carboxyl group, $C_6$–$C_{10}$ aryl group, $C_6$–$C_{10}$ aryloxy group, $C_2$–$C_{10}$ alkenyl group, $C_7$–$C_{40}$ arylalkyl group, $C_7$–$C_{40}$ alkylaryl group, $C_8$–$C_{40}$ arylalkenyl group.

21. A catalytic component having general formula (I):

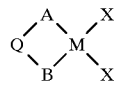

(I)

wherein:

A is a cyclopentadienyl derivative having general formula (II)

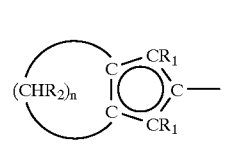

(II)

wherein $R_1$ and $R_2$ are selected from the group consisting of H and $C_1$–$C_3$ alkyl radicals; n is an integer from 2 to 18; B is a monofunctional cyclopentadienyl radical (F) selected from the group consisting of cyclopentadienyl, indenyl, fluorenyl and alkyl, aryl, or trialkylsilyl substituted derivatives;

Q, a bridge between A and B, is a bifunctional radical selected from the group consisting of:
a) a $C_1$–$C_{20}$ alkylene group, linear, branched or cyclic;
b) a silanylene or disilanylene alkyl substituted group; and
c) a silaalkylene alkyl substituted group;

M is selected from the group consisting of titanium, zirconium, hafnium, vanadium and niobium;

X is selected from the group consisting of halogen, hydrogen, $C_1$–$C_{10}$ alkyl group, $C_1$–$C_{10}$ alkoxide group, $C_2$–$C_{20}$ amide group, $C_2$–$C_{20}$ carboxyl group, $C_6$–$C_{10}$ aryl group, $C_6$–$C_{10}$ aryloxy group, $C_2$–$C_{10}$ alkenyl group, $C_7$–$C_{40}$ arylalkyl group, $C_7$–$C_{40}$ alkylaryl group, $C_8$–$C_{40}$ arylalkenyl group.

* * * * *